US007695443B2

(12) United States Patent
Voss

(10) Patent No.: US 7,695,443 B2
(45) Date of Patent: Apr. 13, 2010

(54) DEVICE FOR GENERATING SHOCK WAVES

(75) Inventor: Axel Voss, Kreuzlingen (CH)

(73) Assignee: Tissue Regeneration Technologies, LLC, Woodstock, GA (US)

( * ) Notice: Subject to any disclaimer, the term of this patent is extended or adjusted under 35 U.S.C. 154(b) by 400 days.

(21) Appl. No.: 11/654,805

(22) Filed: Jan. 18, 2007

(65) Prior Publication Data

US 2007/0239084 A1 Oct. 11, 2007

Related U.S. Application Data

(60) Provisional application No. 60/759,989, filed on Jan. 18, 2006.

(30) Foreign Application Priority Data

Jan. 18, 2006 (DE) ....................... 10 2006 002 412

(51) Int. Cl.
*A61B 18/26* (2006.01)

(52) U.S. Cl. ........................... 601/4; 600/437; 600/439; 606/128

(58) Field of Classification Search ................. 600/437, 600/439, 447, 448; 606/128; 601/4
See application file for complete search history.

(56) References Cited

U.S. PATENT DOCUMENTS

| | | | | |
|---|---|---|---|---|
| 4,744,760 | A * | 5/1988 | Molday | 435/7.2 |
| 4,960,107 | A * | 10/1990 | Aida et al. | 601/2 |
| 5,581,192 | A * | 12/1996 | Shea et al. | 324/722 |
| 6,645,144 | B1 * | 11/2003 | Wen et al. | 600/437 |
| 2004/0092819 | A1 * | 5/2004 | Richards | 600/437 |

* cited by examiner

*Primary Examiner*—Long V Le
*Assistant Examiner*—Vani Gupta
(74) *Attorney, Agent, or Firm*—David L King

(57) ABSTRACT

The invention relates to a device for generating shock waves for medical therapy comprising two electrodes of a spark discharge section, wherein the device is filled with a liquid medium, and wherein the liquid medium comprises a colloidal suspension of a conducting, semiconducting, or polarizable substance in water.

2 Claims, 1 Drawing Sheet

DEVICE FOR GENERATING SHOCK WAVES

STATEMENT OF RELATED CASES

Pursuant to 35 U.S.C. 119(a), the instant application claims priority to prior German application number 10 2006 002 412.5, filed Jan. 18, 2006. This application also claims the benefit of U.S. Provisional Application No. 60/759,989, filed Jan. 18, 2006.

FIELD OF THE INVENTION

The invention relates to a device for generating shock waves.

BACKGROUND

Shock wave generators are used in numerous medical fields. The best-known field is the therapeutic and cosmetic application in the treatment for instance of calculous diseases (e.g., urolithiasis, cholelithiasis) and the treatment of scars in human and veterinary medicine.

New fields of application relate to dental treatment, the treatment of arthrosis, the ablation of calcerous deposits (e.g., tendinosis calcarea), the treatment of chronic tennis or golfer elbows (so called radial or ulnar epicondylopathy), of chronic discomfort of the shoulder tendons (so called enthesopathy of the rotator cuff), and of chronic irritation of the Achilles tendon (so called achillodynia).

Furthermore, the generation of shock waves is used in the therapy of osteoporosis, periodontosis, non-healing bone fractures (so called pseudoarthrosis), bone necrosis, and similar diseases. Newer trials investigate the application in stem cell therapy.

Furthermore, the generation of shock waves can be used to exert mechanical stress, e.g., in the form of shearing forces, on cells, wherein their apoptosis is initiated. This happens for example by means of an initiation of the 'death receptor pathway' and/or the cytochrome c-pathway and/or a caspase cascade.

The term apoptosis is understood to refer to the initiation of a genetically controlled program, which leads to the 'cell suicide' of individual cells in the tissue structure. As a result, the cells concerned and their organoids shrink and disintegrate into fragments, the so-called apoptotic bodies. These are phagocytized afterwards by macrophages and/or adjoining cells. Consequently, the apoptosis constitutes a non-necrotic cell death without inflammatory reactions.

Therefore, the application of shock waves is beneficial in all cases, where it relates to the treatment of diseases with an abased rate of apoptosis, e.g., treatment of tumors or viral diseases.

Additionally, the generation of shock waves can be applied beneficially in the treatment of necrotically changed areas or structures in muscle tissue, especially in tissue of the cardiac muscle, in the stimulation of cartilage assembly in arthritic joint diseases, in the initiation of the differentiation of embryonic or adult stem cells in vivo and in vitro in relation to the surrounding cell structure, in the treatment of tissue weakness, especially of cellulitis, and in the degradation of adipose cells, as well as the activation of growth factors, especially TGF-[beta].

Likewise, the generation of shock waves can be used for avoiding the formation and/or extension of edema, for degradation of edema, for the treatment of ischaemia, rheumatism, diseases of joints, jaw bone (periodontosis), cardiologic diseases and myocardial infarcts, pareses (paralyses), neuritis, paraplegia, arthrosis, arthritis, for the prevention of scar formation, for the treatment of scar formation respectively nerve scarring, for the treatment of achillobursitis and other bone necroses.

Another application relates to the treatment of spinal cord and nerve lesions, for example spinal cord lesions accompanied by the formation of edema.

Shock waves are also applicable for the treatment of scarred tendon and ligament tissue as well as badly healing open wounds.

Such badly healing open wounds and boils are called ulcus or also ulceration. They are a destruction of the surface by tissue disintegration at the dermis and/or mucosa. Depending on what tissue fractions are affected, surfacial lesions are called exfoliation (only epidermis affected) or excoriation (epidermis and corium affected).

Open wounds that can be treated with shock waves comprise especially chronic leg ulcers, hypertensive ischaemic ulcers, varicose ulcers or ulcus terebrans due to a thereby caused improved healing process.

Furthermore, shock waves are suitable for the stimulation of cell proliferation and the differentiation of stem cells.

Typical shock wave generators comprise a basis device, to which a therapy head can be connected. The therapy head comprises an integrated reflector with a shock wave source and a coupling membrane.

The therapy head can be made from different materials and must comply with further safety requirement depending on the type of shock source.

The therapy head comprises a connection cable for connecting to a basis device. For the user, the therapy head represents a single unit.

Typically, the therapy heads at the devices are changeable, on the one hand to be able to attach different therapy heads or to be able to detach the therapy head for maintenance or refurbishing work.

The reflector, which is integrated in the therapy head, is at least partially filled with a liquid. The liquid usually comprises a wave impedance corresponding approximately to the wave impedance of the body to be treated. Thereby, an easy coupling of the shock wave into the target object is made possible and losses during the coupling are minimized.

For filling the reflector with liquid or for emptying the liquid the therapy head can comprise valves.

The shock source is typically located in a focus or relatively near to a focus of the reflector.

The shock source is connected to the basis device by a suitable connection via the reflector retainer. The basis device supplies the treatment head with the necessary energy. Depending on the device, the basis device is also counting the number of shocks.

For example, the shock source is a spark discharge section formed by two opposite pointed electrodes. When a voltage (usually in the order of magnitude of about 10 kV to about 30 kV) is applied to these electrodes and the distance between the electrodes is not too large, an electrical breakdown occurs in form of a spark discharge. The latency time, i.e. the time between applying the voltage and the electrical breakdown depends, amongst other things, on the distance of the electrode tips. By wearout of the electrode tips during spark discharge this distance increases with time. If the distance is too large, the breakdown is becoming more and more unreliable until it is no more possible.

EP 0 781 447 B1 describes that conducting, semiconducting, or polarizable particles with a diameter from preferably between a few microns to a few hundred microns are added to the liquid in the reflector, which allow a electrical breakdown between the electrodes even when the distance between the electrode tips becomes so large that no discharge would occur without these particles.

Spark discharge systems comprise so called catalyzer material in their filling which is intended to reduce the bubbles generated during the spark discharge. For example, the catalyzer material can comprise palladium oxide hydrate that can bind hydrogen generated by re-hydrogenation or permeated hydrogen. Since catalyzer materials predominantly are based on noble metals, they are extremely expensive.

The reflector usually is made from stainless steel materials or brass alloys to minimize corrosion of the reflector surface and, at the same time, to have a material as dense as possible at one's disposal, which, at the same time, reflects sound waves.

SUMMARY OF THE INVENTION

It is the object of the present invention to further reduce the latency time of the shock wave generation in order to increase reliability of the shock wave generation.

This object is solved by a device for generating shock waves with two electrodes of a spark discharge section, wherein the device is filled with a colloidal suspension of a conducting, semiconducting, or polarizable substance in water.

Preferably, a colloidal suspension of microscopic aluminum particles in water is used.

A colloidal suspension is usually understood as a dispersion of microscopic solid state particles with a size of 1 nanometer to 1 micron in a liquid medium. The colloid particle are small enough for the Brownian motion to prevent falling of the particles in a gravitational field. Thus, it is ensured that the conducting, semiconducting, or polarizable colloid particles remain between the tips of the electrodes of the spark discharge section.

The mobility of the colloid particles in the liquid medium is very high due to their small size, allowing an easier spark discharge even for large distances of the electrodes.

In a preferred embodiment the device is surrounded by a casing permeable to shock waves and is insertable into the reflector of a shock wave therapy head. The device can be inserted into the therapy head such that the spark discharge section is located on or near the primary focus of the reflector ellipsoid. Thereby the shock waves are optimally focused into the target focus of the ellipsoid.

The connection of the device for generating shock waves to the therapy head can be a screw coupling, a plug coupling, a snap coupling, a bayonet coupling, or a different suitable coupling.

In a further preferred embodiment the device according to the invention is itself designed as a therapy head, thus allowing easier manufacturing, since no additional couplings must be provided. Usage of the therapy head is also facilitated, when no error-prone assembly step must be made by the user. By using a colloidal suspension it is ensured that conducting, semiconducting, or polarizable particles are present between the electrodes of the spark discharge section, even when the volume, inside of which the spark discharge occurs, is very small in comparison with the total volume of the reflector.

Additional substances can be added to the colloidal suspension, for example substances inhibiting the formation of large gas bubbles during spark discharge, by absorbing or bringing to reaction the gases (hydrogen and oxygen) created during the generation of shock waves. Besides or in addition to the palladium compounds mentioned above strong oxidizing and reducing agents can be used, like for example metal crystallites and/or water catalytes. Preferably, the used substances are water soluble and/or are present as a fine powder.

BRIEF DESCRIPTION OF THE DRAWINGS

In the following, the invention will be explained in detail with regard to the drawings.

DETAILED DESCRIPTION OF THE INVENTION

Figure 1:
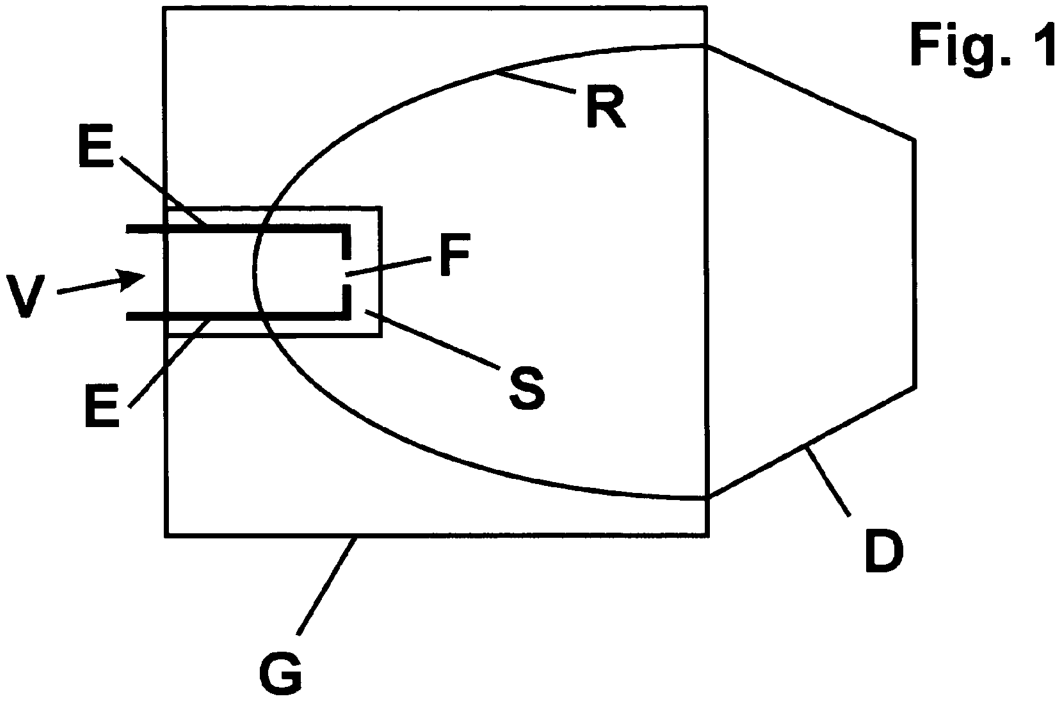
FIG. 1 shows a schematic view of a therapy head for treatment with shock waves with a device for generating shock waves according to the invention.

From the view according to FIG. 1*a* therapy head for treatment with shock waves can be seen into which a device (V) for generating shock waves according to the invention is inserted. The therapy head consists of a housing (G) comprising a reflector (R), which is formed by a cavity that is open in the distal direction. The form of the reflector (R) is essentially rotationally symmetrical and corresponds to a section of an ellipsoid. The open side of the cavity is closed with a closure cap (D) made from a material guaranteeing a good coupling of the shock waves into the body part to be treated, for example from silicone. The thus resulting closed cavity is at least partially filled with a liquid medium, e.g., with water.

On the proximal side of the housing (G) there is a recess into which the device (V) for generating shock waves according to the invention can be inserted such that the spark discharge section (F) is located on or next to the primary focus of the reflector ellipsoid.

The device (V) comprises two electrodes (E), having a spark discharge section (F) between their tips. The distal section of the device (V), where the spark discharge section (F) is located, is filled with a colloidal suspension (S) of conducting particles, e.g., made from aluminum, in water. The dividing wall between the distal section of the device (V) and its proximal section preferably is designed such that the portion of the reflector ellipsoid missing due to the recess is completed.

The distal section of the device (V) is surrounded by a casing consisting of a material guaranteeing a good coupling of the shock waves into the medium inside the reflector cavity. Thus, it is ensured that the shock waves generated by the device (V) in the primary focus of the reflector (R) are focused into the target focus inside the body of the patient.

The housing (G) with the inserted device (V) can be inserted into a therapy head retainer (not shown) such that the electrodes (E) of the device (V) come into electrical contact with the control electronics (not shown).

Figure 2:
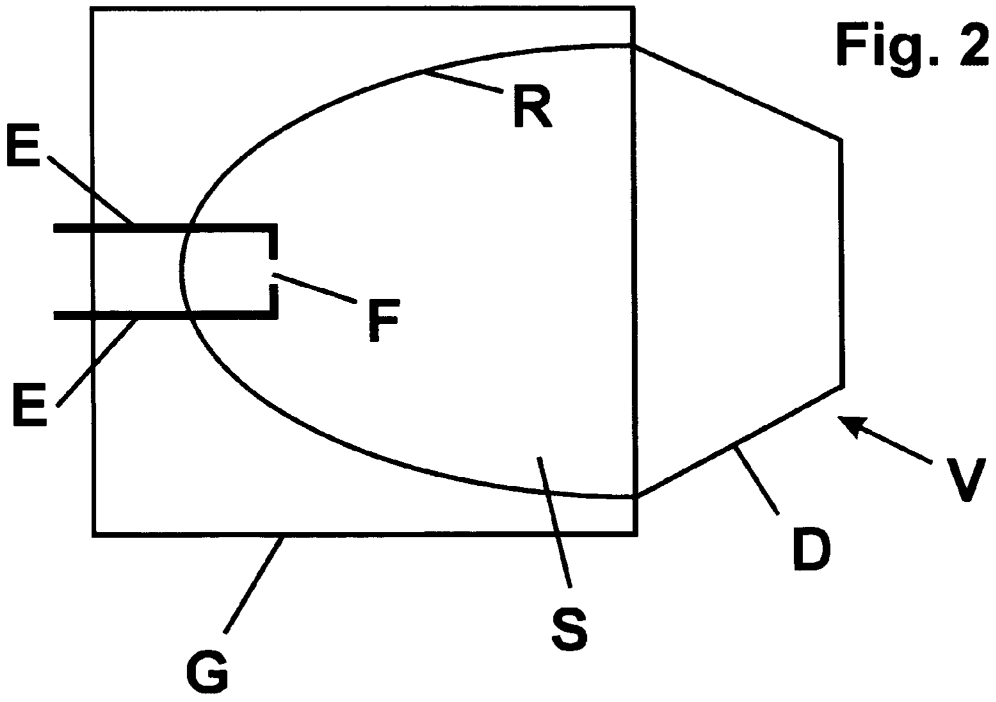
FIG. 2 shows a schematic view of a therapy head for treatment with shock waves which is designed as a device for generating shock waves according to the present invention.

FIG. 2 shows an alternative embodiment of the device (V) for generating shock waves according to the invention. In this embodiment, the device (V) is designed as shock waves therapy head and does not need to be inserted into the therapy head, as in the embodiment according to FIG. 1. The two electrodes (E), between the tips of which the spark discharge section (F) is located, are fixedly connected to the housing (G) such that the spark discharge section (F) is located on or next to the primary focus of the reflector ellipsoid.

The cavity formed by the housing (G) and closure cap (D), which is made from a material guaranteeing a good coupling of the shock waves into the body part to be treated, e.g., from silicone, is at least partially filled with a colloidal suspension (S) of conducting particle, e.g., from aluminum, in water.

The device (V) designed as a therapy head can also be inserted into a therapy head retainer (not shown) such that the electrodes (E) of the device (V) come into electrical contact with the control electronics (not shown).

LIST OF REFERENCE SIGNS

D closure cap
E electrode
F spark discharge section
G housing
R reflector
S colloidal suspension
V device for generating shock waves

We claim:

1. A therapy head for treatment with shock waves into which is inserted device (V) for generating acoustic shock waves for medical therapy when an applied voltage of 10 KV to about 30 KV is applied to generate a spark discharge the therapy head comprising a housing having a reflector (R) which is formed having a cavity that has an open side in the distal direction;

a closure cap (D) made from a material for coupling the shock waves into the body part to be treated, the closure cap (D) closes the open side of the reflector sealing the cavity; and wherein the device (V) is inserted into a recess on a proximal side of the housing, the device (V) having two electrodes of a spark discharge section extending into the cavity, which generates a spark discharge under exposure to 10 KV to 30 KV at on or near a focus of the reflector wherein the cavity is filled with a liquid medium, and wherein the liquid medium comprises a colloidal particle suspension of a conducting, semiconducting, or polarizable substance of aluminum particles in water which reduces the latency time of the shock wave generation wherein the aluminum particles are of a size of 1 nanometer to 1 micron to prevent falling of the particles in a gravitational field thereby maintaining a portion of the colloidal particle suspension between the two electrodes.

2. The device according to claim 1, wherein the diameter of the particles of the conducting, semiconducting, or polarizable substance of particles is smaller than 1 micron.

* * * * *